United States Patent [19]
Yang

[11] Patent Number: 5,376,737
[45] Date of Patent: Dec. 27, 1994

[54] METHODS FOR BENEFITTING POLYMERS

[75] Inventor: Shih-Liang S. Yang, Laguna Hills, Calif.

[73] Assignee: Allergan, Inc., Irvine, Calif.

[21] Appl. No.: 959,394

[22] Filed: Oct. 9, 1992

Related U.S. Application Data

[63] Continuation-in-part of Ser. No. 691,149, Apr. 25, 1991, Pat. No. 5,164,462.

[51] Int. Cl.$^5$ ............................................... C08G 77/38
[52] U.S. Cl. .................................... 525/477; 525/478
[58] Field of Search ................................ 525/477, 478

[56] References Cited

U.S. PATENT DOCUMENTS

| | | | |
|---|---|---|---|
| Re. 33,477 | 12/1990 | Loshaek | 351/160 |
| 4,213,892 | 7/1980 | Scott | 524/289 |
| 4,250,268 | 2/1981 | Rody et al. | 525/100 |
| 4,316,033 | 2/1982 | Ching | 524/91 |
| 4,380,643 | 4/1983 | Yoshida et al. | 548/259 |
| 4,415,687 | 11/1983 | Avar et al. | 524/102 |
| 4,528,311 | 7/1985 | Beard et al. | 351/160 |
| 4,555,545 | 11/1985 | Kimura et al. | 528/29 |
| 4,608,050 | 8/1986 | Wright et al. | 128/1 |
| 4,612,358 | 9/1986 | Besecke et al. | 526/259 |
| 4,803,254 | 2/1989 | Dunks et al. | 525/477 |
| 4,868,251 | 9/1989 | Reich et al. | 525/478 |
| 4,872,877 | 10/1989 | Tiffany | 351/160 R |
| 4,960,898 | 10/1990 | Sakuta et al. | 548/110 |
| 5,077,340 | 12/1991 | Ravichandran et al. | 525/203 |
| 5,102,707 | 4/1992 | Canivenc et al. | 548/110 |
| 5,145,893 | 9/1992 | Galbo et al. | 524/102 |

FOREIGN PATENT DOCUMENTS

| | | |
|---|---|---|
| 0282294 | 9/1988 | European Pat. Off. . |
| 0388218 | 9/1990 | European Pat. Off. . |
| 0434619A2 | 6/1991 | European Pat. Off. . |
| 0488145A2 | 6/1992 | European Pat. Off. . |
| 02-051542 | 2/1990 | Japan . |
| WO86/04342 | 7/1986 | WIPO . |
| WO88/04299 | 6/1988 | WIPO . |

OTHER PUBLICATIONS

Contact Lenses, A Clinical Approach to Fitting, Robert H. Hales, 59, 199-204(1978).
Contact Lens Handbook, James R. Lee, 5, 28-32, 70, 71, 117.

Primary Examiner—Veronica P. Hoke
Attorney, Agent, or Firm—Frank J. Uxa, Jr.; Gordon L. Peterson

[57] ABSTRACT

Methods for incorporating beneficial components into polymeric materials are disclosed. In one embodiment, the method comprises introducing a reactable UV light absorbing component into a cross-linked and/or solid polymeric material containing reactable groups, and subjecting the reactable UV light absorbing component to conditions effective to chemically react the reactable UV light absorbing component with the reactable groups of the solid polymeric material.

17 Claims, No Drawings

METHODS FOR BENEFITTING POLYMERS

RELATED APPLICATION

This application is a continuation-in-part of application Ser. No. 691,149, filed Apr. 25, 1991, now U.S. Pat. No. 5,164,462, which is incorporated in its entirety herein by reference.

BACKGROUND OF THE INVENTION

This invention relates to methods for benefitting polymeric materials. More particularly, this invention relates to methods for incorporating beneficial components, for example, ultraviolet (UV) light absorbing components into polymeric materials, for example, into silicone polymers, to provide effectively benefitted polymer materials useful, for example, as lenses.

The incident light entering the eye is composed of the entire spectrum of wavelengths including the ultraviolet, visible, and infrared. The cornea preferentially filters UV light in the range of about 300 nm to about 400 nm. Thus, in the eye with its natural lens in place relatively little radiation of wavelengths less than about 400 nm reaches the posterior intraocular structures, e.g., the vitreous humor and the retina.

In the aphakic individual, i.e., that individual who has had the natural crystalline lens removed, there is a loss in protection for the retina from UV light in the above-noted range. Thus, the use of UV absorbing contact or intraocular lenses is particularly important for the aphakic person. It is further believed that UV light screening spectacles or contact lenses may retard the development of a cataract in the natural lens.

Although low molecular weight, non-polymerizable UV light absorbing compounds of various types are relatively easy to compound into polymer formulations and are effective in blocking UV radiation when compounded into polymer formulations, their extractability in various media may limit their utility. This extractability problem has been remedied by the synthesis of polymerizable, UV light absorbing monomers which conventionally are combined prior to polymerization with the other polymerizable monomers. This monomer blend is then subjected to polymerization conditions effective to form the polymer product. These covalently bonded UV light absorbing constituents are not extractable and do not phase separate from the remainder of the polymer.

Examples of polymerizable UV light absorbing components which may be incorporated into monomer blends prior to polymerization include the vinylsilylalkoxy arylbenzotriazole monomers disclosed in Dunks et al U.S. Pat. No. 4,803,254; the benzotriazole derivatives disclosed in Reich et al U.S. Pat. No. 4,868,251, Yoshida et al U.S. Pat. No. 4,380,643, Beard et al U.S. Pat. No. 4,528,311 and Besecke et al U.S. Pat. No. 4,612,358; and the benzophenone derivatives disclosed in Loshaek U.S. Pat. No. RE. 33,477 and Reich et al U.S. Pat. No. 4,868,251. The disclosure of each of these patents is incorporated in its entirety by reference herein.

One problem with the conventional methods of forming a polymer from a monomer mix including a polymerizable UV light absorbing monomer is that the UV light absorbing monomer may have an adverse effect or impact on the polymerization reaction, or on the other properties of the final polymer. Also, it may be somewhat difficult to combine the desired amount of UV light absorbing monomer with the remainder of the monomers prior to polymerization in order to achieve the desired UV light absorbing properties.

Clearly, it would be advantageous to provide new methods for incorporating UV light absorbing components, and other beneficial components, into polymer materials.

SUMMARY OF THE INVENTION

New methods for incorporating beneficial components into polymer materials have been discovered. The present methods provide for the simple and straight-forward inclusion of beneficial constituents, in polymer materials without the necessity of combining a polymerizable beneficial component or monomer, for example, a polymerizable UV light absorbing monomer, with other monomers prior to the polymerization reaction. In effect, a polymeric material, preferably a cross-linked and/or solid polymeric material, is formed prior to introducing the beneficial component into the polymeric material. In this manner, the desired properties and characteristics of the polymeric material are obtained by controlled polymerization of the monomer or monomers other than the additional beneficial component. Polymeric materials which are very well suited for their intended purpose, for example, for the production of ophthalmic devices, such as corneal contact lenses, intraocular lenses, and corneal intrastromal implant lenses, are obtained without interference or other adverse impact from the presence of the beneficial component during polymerization.

In accordance with the present invention, the beneficial component, such as the UV light absorbing component, is incorporated in the polymer material in an easily controlled manner so as to provide the desired benefit to the polymer material, without significantly detrimentally affecting the other desirable properties of the polymer material.

In one broad aspect, the present methods incorporating a beneficial component into a polymer material comprise introducing a reactable beneficial component into a polymeric material, preferably a cross-linked and/or solid polymeric material, containing reactable groups. The reactable beneficial component is subjected to conditions effective to chemically react the reactable beneficial component with the reactable groups of the polymeric material, thereby forming a polymer material, preferably a cross-linked and/or solid polymer material, to which is bonded, preferably covalently bonded, a beneficial constituent derived from the beneficial component in an amount effective to provide a benefit to the polymer material. The benefit provided is relative to the polymeric material prior to the inclusion of the beneficial constituent.

In a particularly useful embodiment, methods for incorporating a UV light absorbing component into a polymer material are provided. These methods comprise introducing a reactable UV light absorbing component into a polymeric material, for example, a cross-linked and/or solid polymeric material, containing reactable groups. The reactable UV light absorbing component is subjected to conditions effective to chemically react the reactable UV light absorbing component with the reactable groups of the polymeric material. A polymer material including an effective amount of a UV light absorbing constituent derived from the reactable UV light absorbing component covalently bonded thereto is preferably provided.

DETAILED DESCRIPTION OF THE INVENTION

The present invention is applicable to benefitting any polymer which includes reactable groups, even unwanted reactable groups. Thus, in one embodiment, the benefit obtained in accordance with the present invention is a decrease in the reactability, for example, in the number of reactable groups, of the polymeric material.

Any polymeric material, for example, any cross-linked and/or solid polymeric material, which includes reactable groups may be processed in accordance with the present invention.

As used herein, the term "reactable groups" refers to substituents on the polymeric material which are capable of being reacted with the reactable beneficial component, for example, the reactable UV light absorbing component, being employed. Examples of such reactable groups include hydride groups, groups which include carbon-carbon unsaturation, hydroxyl groups, carboxyl groups, amine groups, other carbon-containing groups, other nitrogen-containing groups, phosphorus-containing groups, sulfur-containing groups, halogen-containing groups, and the like and mixtures thereof. The present invention is particularly applicable when the reactable groups in the polymeric material are selected from hydride groups and groups containing carbon-carbon unsaturation, more preferably when the reactable groups are hydride groups. Such reactable groups may be, and often are, the same type of groups which are reacted to form the polymeric material. Thus, the polymeric material may be said to include residual reactable groups.

The base polymeric materials which may be used in the present methods may be chosen from any suitable such materials, provided that reactable groups are included. The presently useful polymeric materials may be hydrocarbon-based polymeric materials, may be silicone polymeric materials, or may be one or more other types of polymeric materials. The polymeric material is preferably cross-linked and/or is present in the solid phase prior to being exposed to the reactable beneficial component in accordance with the present invention. In a particularly useful embodiment, the present processing to incorporate a beneficial constituent (derived from the reactable beneficial component) into the polymer material does not substantially increase or decrease the degree of polymerization or cross-linking of the polymeric material. The present processing preferably has little or no effect, other than to provide the desired benefit from the incorporation of the beneficial constituent, on the properties of the final polymer material. The polymer material produced in accordance with the present process is preferably utilized, for example, as a lens material, such as a foldable intraocular lens material, without further substantial polymerization or cross-linking.

The reactable beneficial component is chosen to (1) yield a beneficial constituent which provides the desired benefit to the polymer material when incorporated into the polymer material; and (2) to react with the reactable groups present in the polymeric material. Although any such beneficial component may be employed, for clarity and brevity, the description hereinafter refers to the beneficial component as being a UV light absorbing component. It should be noted that providing polymer materials, particularly polymer materials which are optically clear and are useful for ophthalmic devices, such as corneal contact lenses, intraocular lenses, corneal intrastromal lenses and the like, with UV light absorbing properties is one important application of the present invention.

In one embodiment, the present invention relates to methods for incorporating a UV light absorbing component into a polymer material. These methods comprise introducing a reactable UV light absorbing component into a polymeric material, preferably a cross-linked and/or solid polymeric material, containing reactable groups; and subjecting the reactable UV light absorbing component to conditions effective to chemically react the reactable UV light absorbing component with the reactable groups of the polymeric material. Such subjecting is preferably effective to form a polymer material, preferably a cross-linked and/or solid polymer material, to which is covalently bonded a UV light absorbing constituent derived from the reactable UV light absorbing component.

The introducing and subjecting steps of the present methods are preferably effective to distribute the UV light absorbing constituent substantially uniformly throughout the polymer material.

The reactable UV light absorbing component can be introduced into the polymeric material combined with a liquid carrier, for example, in the form of a suspension or dispersion in a liquid medium or, and preferably, in the form of a solution. The liquid medium or solvent should be selected to be compatible with (i.e., have no undue detrimental effect on) the reactable UV light absorbing component and the polymeric material, and is preferably such that it can be easily removed from the polymeric material or the polymer material. A particularly useful class of liquid carriers when siloxane polymers are involved are hydrocarbon-based materials, such as tetrahydrofuran, hexane and the like, in particular aromatic hydrocarbon-based materials, for example, toluene and the like.

Alternately, if the reactable UV light absorbing component can be vaporized, for example, at reduced pressures, such component can be introduced into the polymeric material in the vaporous or gaseous state.

The amount of reactable UV light absorbing component introduced into the polymeric material should be sufficient to provide the desired benefit, e.g., UV light absorbing properties, to the polymer material. Some excess of reactable UV light absorbing component may advantageously be introduced to facilitate, for example, increase, the rate at which the reactable UV light absorbing component reacts with the reactable groups of the polymeric material. The amount of UV light absorbing constituent included in the final polymer material varies widely depending on the specific UV light absorbing constituent involved and the degree of benefit desired. For example, the amount of the UV light absorbing constituent in the polymer material can range from about 0.1% or less to about 1% or about 5% or about 10% or more, by weight.

In any event, the reactable UV light absorbing component which is introduced into the polymeric material is subjected to conditions effective to chemically react this reactable UV light absorbing component with the reactable groups of the polymeric material to form a UV light absorbing constituent in the resulting polymer material which is derived from the reactable UV light absorbing component. Preferably, the UV light absorbing constituent is covalently bonded into the polymer material. In this manner, the polymer material is rendered UV light absorbing.

The introducing and subjecting steps of the present invention can occur sequentially (introducing before subjecting) or simultaneously or a combination thereof, for example, with these two steps occurring at least partially simultaneously and the subjecting step continuing after the introducing step is concluded.

The conditions at which the above-noted subjecting step occurs are chosen to provide the desired final product. These conditions are preferably such that the polymeric material and final polymer material suffer no substantial detrimental effects. For example, such conditions are preferably selected so that no substantial increase or decrease in the degree of polymerization or the degree of cross-linking of the polymeric material occurs. Often, such conditions are selected to maintain the polymeric material and final polymer material in a solid state. Temperatures are preferably in the range of about 0° C to about 150° C., more preferably in the range of about 20° C. to about 100° C. or about 110° C. Subjecting times may vary widely. For example, times on the order of 0.1 or about 0.5 hours or less to about 70 hours or more may be employed. Particularly useful results are obtained where the subjecting time is in the range of about 2 hours or about 4 hours to about 12 hours to about 24 hours.

The subjecting step is preferably catalyzed or promoted so as to facilitate the covalent bonding of the UV light absorbing constituent to the polymer material. Although an effective amount of a suitable separate or additional catalyst or promotor can be incorporated into the polymeric material before and/or during the subjecting step, it has unexpectedly been found that the catalyst or promotor used to facilitate the formation of the polymeric material, which is present in the polymeric material, is often effective to promote the covalent bonding of the UV light absorbing constituent to the polymer material. Such "residual" catalysis is very convenient, for example, requiring that no separate or additional catalyst or promotor be used, and provides for effective UV light absorbing constituent/polymer material covalent bonding at relatively mild conditions. Conducting the present subjecting step at mild or low severity conditions also reduces the risks that the polymer material will be detrimentally affected by such processing.

A particularly useful class of polymerization catalysts which also can act to promote the UV light absorbing constituent/polymer material covalent bonding is the platinum group metal-containing components, preferably platinum-containing components, utilized in promoting polymerization, for example, the formation of silicone polymers. Many platinum group metal-containing components are conventional and well known as polymerization catalysts.

The platinum group metal-containing components have been found to be particularly effective when the reactable UV light absorbing component includes a functional group selected from hydride groups or functional groups containing carbon-carbon unsaturation and the reactable groups of the polymeric material are selected from the other of such groups. For example, if the reactable UV light absorbing component includes a functional group containing carbon-carbon unsaturation, the reactable groups of the polymeric material are hydride groups, and vice versa.

After the subjecting step, the resulting polymer material may be processed to remove any free or unreacted reactable UV light absorbing component. For example, this polymer material may be extracted with one or more non-interfering or compatible materials to extract the free reactable UV light absorbing component from the polymer material. The remaining UV light absorbing constituent is effective to provide the desired UV light absorbing properties to the polymer material.

The final polymer material is then processed, e.g., using conventional techniques, into a useful product. For example, conventional lens manufacturing and/or finishing techniques can be employed to produce a corneal contact lens, intraocular lens or corneal intrastromal lens having effective UV light absorbing properties from the presently derived final polymer material. The present invention is particularly applicable in situations in which the physical/optical properties of the polymer materials should be closely controlled in order to achieve a useful product. One specific example of such a situation is the formation of a foldable intraocular lens, that is an intraocular lens which is deformable for insertion through a small, e.g., about 3 mm in length, surgical incision. The configuration of the foldable IOL, in particular the optical resolution of the foldable IOL, should return completely in a reasonable time after the lens is placed in the eye. Thus, a foldable IOL should be made of a material which is elastomeric and has consistent and homogeneous composition throughout the cross-linked network polymeric structure.

The present invention allows a polymeric material to be produced under closely controlled conditions without the interference of the UV light absorbing component. The resulting polymeric material is formable into a foldable intraocular lens. This polymeric material is treated in accordance with the present invention to provide it with an effective amount of UV light absorbing constituent. The other physical/optical properties of the polymer material are unchanged so that the polymer material with the UV light absorbing constituent can be readily formed into a foldable intraocular lens.

Although any type of polymeric material with reactable groups may be employed, the present invention is particularly applicable to silicone polymeric materials. Specific examples of useful silicone polymeric materials are those materials identified as cross-linked silicone elastomers derived from vinyl functional siloxane base polymers (or prepolymers) and hydride functional cross-linking agents or components. In one embodiment, such base polymers have the following structure or formula:

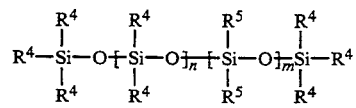

and mixtures thereof, wherein each $R^4$ and $R^5$ is independently selected from the group consisting of H, $CH=CH_2$, alkyl radicals, substituted alkyl radicals, alkoxy radicals, substituted alkoxy radicals, alkenyl radicals with a terminal double bond, substituted alkenyl radicals with a terminal double bond, aryl radicals, substituted aryl radicals and fluoro radical, provided that at least one, and preferably at least two, of the $R^4$s is selected from H and olefinically unsaturated groups; and n and m each is an integer independently selected from integers in the range of 0 to about 20,000. In the event that one or more $R^4$s and/or $R^5$s are fluoro radicals, one or more other $R^4$s and/or $R^5$s are preferably organic radicals. One or more of the $R^4$s and/or $R^5$s may be organo fluoro radicals, for example, fluoro hydrocarbon radicals. In one embodiment, each of the $R^4$s, other than those which are selected from H and olefinically unsaturated groups, and the $R^5$s is methyl. Each of the R4s and $R^5$s may be independently selected from alkyl radicals containing 1 to about 4 carbon atoms, fluoro alkyl radicals containing 1 to about 3 carbon atoms, phenyl radicals, substituted aryl radicals, alkenyl radicals containing 2 to about 4 carbon atoms and having a terminal double bond and mixtures thereof.

Examples of useful alkenyl groups include ethenyl, propenyl, butenyl, hexenyl, octenyl and the like.

The cross-linking or cross-linker agents useful with such base pre-polymers are preferably components of a two part, silicone elastomer formulation, more preferably a two part, platinum catalyzed vinyl/hydride, addition cured silicone elastomer formulation. Thus, when the base pre-polymer is vinyl functional, the cross-linking agent is hydride functional. In addition, one or more of the base pre-polymer and the cross-linking agent can be both vinyl and hydride functional.

In any event, the silicone elastomer is cross-linked and optically clear. These optically clear elastomeric compositions are very effective for inclusion in corneal contact lenses, intraocular lenses and corneal intrastromal lenses. Conventional lens forming techniques, for example, molding techniques, can be used to provide lenses or lens blanks from such elastomeric compositions. These lenses or lens blanks are then processed in accordance with the present invention to provide the desired UV light absorbing properties.

The preferred siloxane cross-linking agents include a plurality of, for example, at least three (3), functional groups per molecule.

Suitable cross-linking agents include agents which are conventionally used to produce cross-linked silicone polymers, in particular, polysiloxane elastomers, for example, employing two part platinum catalyzed silicone systems to produce silicone elastomers by vinyl/hydride addition curing. Thus, suitable cross-linking agents are available as a component of many such conventional two part systems. Specific examples of effective cross-linking agents include 1,3,5,7-tetramethylcyclotetrasiloxane, methyl hydropolysiloxane, 1,3,5-trivinyl-1,1,3,5,5-pentamethyl-trisiloxane, methyl vinyl polysiloxane and the like.

The relative amounts of base pre-polymer and cross-linking agent employed to produce the siloxane elastomer composition are chosen to provide a cross-linked polymeric material having the desired properties, including the desired degree of cross-linking. The relative amounts of the components utilized varies depending on many factors, for example, on the specific components being employed, and on the application for which the polymeric material is to be employed. As noted above, conventional two part silicone polymer formulations can be employed.

In a particularly useful embodiment of the present invention, the ratio of monomers (or prepolymers) used to produce the polymeric material is chosen to provide a predetermined concentration of reactable groups in the polymeric material. This predetermined concentration is preferably greater than the concentration of reactable groups in a substantially identical polymeric material for use without further processing in accordance with the present invention. Such greater concentration of reactable groups advantageously facilitates the chemical reaction of the reactable beneficial component with the reactable groups of polymeric material. However, any adjustments to the conventional two part silicone polymer formulations (in terms of relative amounts of components) are relatively minor (if required at all). For example, if the conventional weight ratio of part A to part B is 1:1, such ratio is preferably adjusted if at all, to be within the range of about 0.75:1 to about 1 to 0.75 to facilitate incorporation of the UV light absorbing constituent.

Any reactable UV light absorbing component may be used in accordance with the present invention. It is important, however, that the reactable UV light absorbing component be selected so as to be capable of reacting with the reactable groups present in the polymeric material.

Particularly useful reactable UV light absorbing components are selected from benzotriazole derivatives, benzophenone derivatives, and the like, and mixtures thereof. Examples of such derivatives are set forth in the patents noted previously and incorporated by reference herein. Because of their outstanding UV light absorbing capabilities, benzotriazole derivatives are particularly useful.

In one particularly useful embodiment, the reactable UV light absorbing components are selected from compounds having the following structure or formula.

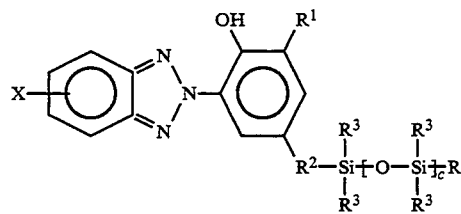

and mixtures thereof, wherein X is selected from the group consisting of H, alkoxy radicals, preferably containing 1 to about 6 carbon atoms, and halogen; $R^1$ is selected from the group consisting of H and alkyl radicals, preferably containing 1 to about 8, more preferably 1 to about 4 carbon atoms, provided that at least one of X and $R^1$ is other than H; $R^2$ is selected from divalent hydrocarbon radicals such as alkylene radicals, divalent substituted hydrocarbon radicals, oxo, divalent oxyhydrocarbon radicals and divalent substituted oxyhydrocarbon radicals, preferably containing up to about 6 carbon atoms and more preferably containing 1 to about 4 carbon atoms, and still more preferably being an alkylene radical containing 1 to about 4 carbon atoms; each $R^3$ is independently selected from alkyl radicals, substituted alkyl radicals, alkoxy radicals, substituted alkoxy radicals, aryl radicals, substituted aryl radicals, and fluoro radical, preferably from alkyl radicals, alkoxy radicals and aryl radicals and more preferably from alkyl radicals and aryl radicals; R is selected from, H and CH=$CH_2$; and c is an integer in the range of 1 to about 10, preferably 1 to about 4. One or more of the $R^3$s may be organo fluoro radicals, for example, fluoro hydrocarbon radicals. In the event the UV light absorbing compound is polymerizable, R is selected from H and CH=$CH_2$.

In the event that any $R^3$ is aliphatic, it preferably contains 1 to about 8, more preferably 1 to about 4, carbon atoms. If any R is aromatic, it preferably contains 6 to about 10, and more preferably 6, carbon atoms. In a particularly useful embodiment, each $R^3$ is independently selected from methyl radicals, substituted methyl radicals, phenyl radicals and substituted phenyl radicals. In the event that $R^1$ is alkyl, it is preferably tertiary alkyl, and more preferably t-butyl.

Examples of useful alkoxy radicals include methoxy, ethoxy, propoxy, butoxy, hexoxy and the like. A particularly useful halogen group for use as x is chloro. Examples of useful alkyl groups include methyl, ethyl, propyl, butyl, hexyl, octyl and the like. Examples of useful alkylene groups include ethylene, propylene, butylene and the like. Examples of useful aryl radicals include phenyl, methyl phenyl, ethyl phenyl, dimethyl phenyl and the like. The substituted groups referred to herein are exemplified by the above-noted groups (and the other groups referred to herein) substituted with one or more substituent groups including elements such as oxygen, nitrogen, carbon, hydrogen, halogen, sulfur, phosphorus and the like and mixtures or combinations thereof.

A particularly useful class of UV light absorbing compounds is selected from compounds having the following formula or structure

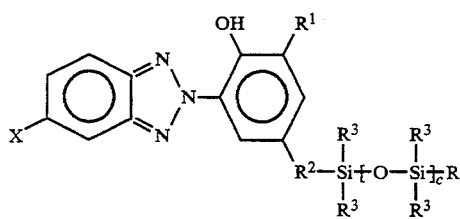

All tautomers, isomers and the like and mixtures thereof of the presently useful UV light absorbing components are included within the scope of the present invention.

The above-noted hydride functional UV light absorbing compounds can be prepared, for example, using the vinyl functional, benzotriazole derivatives disclosed in Reich et al U.S. Pat. No. 4,868,251 as starting materials. It should be noted that the benzotriazole derivatives disclosed in this Reich et al patent are also very effective for use in the present invention. Such vinyl functional, benzotriazole derivative is reacted with a siloxane having at least two functional hydride groups if the UV light absorbing compound is to be polymerizable or with a siloxane having only one functional hydride group if a non-polymerizable UV light absorbing compound is to be produced. This reaction preferably occurs in the liquid phase, using a conventional solvent such as toluene, in the presence of a catalyst, such as a platinum-containing catalyst. Reaction conditions are sufficient to allow the vinyl group of the benzotriazole derivative to react with one of the hydride groups (or the only functional hydride group) of the siloxane. Such conditions can include a temperature in the range of about $-60°$ C. to about $50°$ C. and reaction times in the range of about 1 hour or less to about 60 hours or more. The resulting hydride functional UV light absorbing monomer or monomers or non-polymerizable UV light absorbing compound or compounds can be recovered, separated and/or purified using conventional techniques, such as distillation, extraction and the like.

The present hydride functional UV light absorbing monomers can be used to prepare the present vinyl functional UV light absorbing monomers. Thus, such hydride functional monomers can be reacted with acetylene to form the present vinyl functional monomers. This reaction preferably occurs in the liquid phase, using a conventional solvent such as toluene, in the presence of a catalyst, such as a platinum-containing catalyst. Reaction conditions are sufficient to allow the hydride group of the hydride functional monomer to react with the acetylene. Such conditions can include a temperature in the range of about $-60°$ C. to about $50°$ C. and reaction times in the range of about 0.2 hours or less to about 10 hours or more. The resulting vinyl functional UV light absorbing monomer or monomers can be recovered, separated and/or purified using conventional techniques, such as distillation, extraction and the like.

The use of reactable UV light absorbing components which include at least one silicon atom, preferably at least one siloxane moiety, is particularly advantageous since the presence of such silicon atom (siloxane moiety) is often effective to increase the compatibility of the reactable UV light absorbing component with the silicone polymer, for example, relative to a substantially identical reactable UV light absorbing component without at least one silicon atom (siloxane moiety). Such enhanced compatibility provides for increased ease in obtaining a substantially uniform distribution of the UV light absorbing constituent in the final solid polymer material.

The following non-limiting examples illustrate certain aspects of the present invention.

The starting material in Example 1 is 2-(2'-hydroxy-3'-t-butyl-5'-vinylphenyl)-5-chloro-2H-benzotriazole, hereinafter referred to as "I" or UV-4, which itself can be produced as described in Reich et al U.S. Pat. No. 4,868,251.

EXAMPLE 1

Preparation of
2-[3'-t-butyl-2'-hydroxy-5'-(2''-(7'''-hydro octamethyl tetrasiloxane)ethyl) phenyl]-5-chloro2H-benzotriazole and 2-[3'-t-butyl-2'-hydroxy-5'-(1''-7'''-hydro octamethyl tetrasiloxane)ethyl) phenyl]-5-chloro-2H-benzotriazole mixture The above-noted mixture of the present UV light absorbing monomers is prepared to be used in preparing the mixture of UV light absorbing monomers in Example 2.

A 100 ml 3 neck flask equipped with a magnetic stirring bar, an inert gas inlet topped reflux condenser and a thermocouple was charged with 20 g (0.071 mole) 1,1,3,3,5,5,7,7-octamethyltetrasiloxane (from Petrarch Systems, Inc.), 4.0 g (0.012 mole) of I and 10 g dry toluene. The mixture was stirred at room temperature for 1 hour until all of the I dissolved. 1 ml platinum complex solution (Petrarch Systems, Inc., catalog no. PC-075) was added and the reaction mixture was stirred at room temperature for 48 hours. Unreacted octamethyltetrasiloxane and toluene were removed by vacuum. 7.5 g (100%) yellow viscous oil, hereinafter identified as "II" was isolated. Using conventional chromatography techniques, II can be further purified, if desired. However, this yellow viscous oil, without further purification, is effective as a polymerizable UV light absorbing monomer mixture. This mixture remained as a liquid even at −60° C.

Mass spectroscopy analysis indicated a molecular weight for II of 610. High pressure liquid chromatography analysis showed essentially two components corresponding to the IIa (80%) and IIb (20%) isomers, shown below. The structures of IIa and IIb isomers and the corresponding concentration ratio were confirmed by UV/VIS, IR, and ¹H NMR analyses.

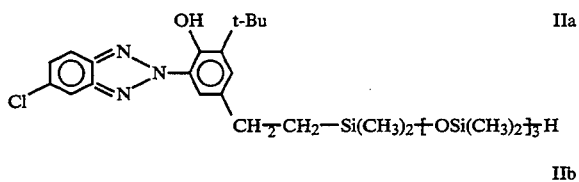

IIa

CH₂—CH₂—Si(CH₃)₂—[OSi(CH₃)₂]₃H

IIb

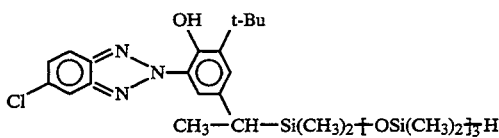

CH₃—CH—Si(CH₃)₂—[OSi(CH₃)₂]₃H

This mixture is found to have very effective UV light absorbing properties.

EXAMPLE 2

Preparation of a 2-[3'-t-butyl-2'-hydroxy-5'-(2''-(7'''-vinyl octamethyl tetrasiloxane) ethyl) phenyl]-5-chloro-2H-benzotriazole and 2-[3'-t-butyl-2'-hydroxy-5'-(1''-(7'''-vinyl octamethyl tetrasiloxane) ethyl) phenyl] 5-chloro-2H-benzotriazole mixture.

A 100 ml, 3 neck flask equipped with a magnetic stirring bar, a reflux condenser, an acetylene gas inlet, and a thermocouple was charged with 2 g of II (the mixture of isomers) and 60 ml dry toluene. The mixture was stirred at room temperature for 10 minutes until all II dissolved. The solution was purged with dry, scrubbed acetylene gas for 2 hours. 1 ml platinum complex solution was added. The reaction mixture was stirred and purged with acetylene continuously at room temperature for 6 hours. Unreacted acetylene and toluene were removed by vacuum. 2.0 g (100%) yellow viscous oil, hereinafter identified as "III", was isolated. Using conventional chromatography techniques, III can be further purified, if desired. However, this isolated product is effective as a polymerizable UV light absorbing monomer mixture. This mixture remained as a liquid even at −60° C.

Mass spectrometry analysis indicated a molecular weight for III of 636. High pressure liquid chromatography analysis showed two components corresponding to the IIIa (80%) and IIIb (20%) isomers, shown below. The structures of the IIIa and IIIb isomers and the corresponding concentration ratio were confirmed by UV/VIS, IR, and ¹H NMR analyses.

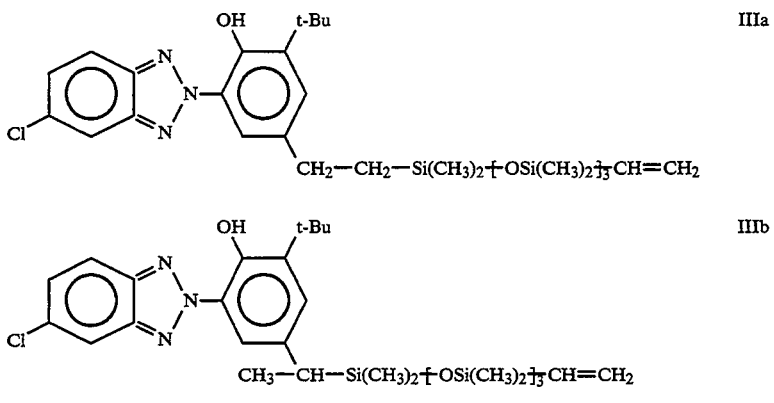

This mixture is found to have very effective UV light absorbing properties.

EXAMPLE 3

Preparation of a 2-[3't-butyl-2'hydroxy-5'-(2''-(5'''-vinyl tetramethyl disiloxane) ethyl) phenyl]-5-chloro-2H-benzotriazole and 2-[3'-t-butyl-2'-hydroxy-5'-(1''-(5'''-vinyl tetramethyl disiloxane) ethyl) phenyl]-5-chloro-2H-benzotrizole mixture.

Examples 1 and 2 are repeated except that tetramethyldisiloxane (from Petrach Systems, Inc.) was used (in the same molar amount) in place of 1,1,3,3,5,5,7,7-octamethyltetrasiloxane.

High pressure liquid chromatography analysis showed essentially two components corresponding to the IVa (about 80%) and IVb (about 20%) isomers, shown below. The structures of IVa and IVb isomers and the corresponding concentration ratio were confirmed by UV/VIS, IR and ¹H NMR analyses.

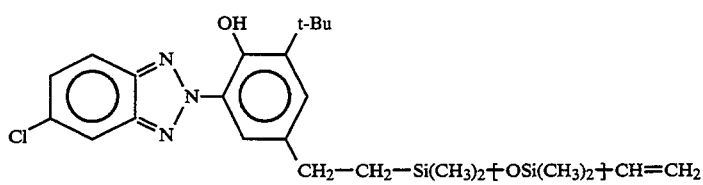

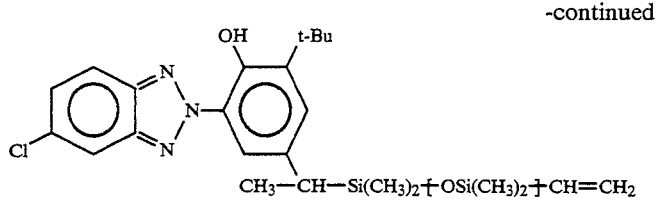

IVb

This mixture is found to have very effective UV light absorbing properties.

EXAMPLE 4

A slab of a conventional platinum-catalyzed, addition cure, cross-linked polyorganosiloxane polymer was provided. This optically clear polymer slab was derived from a conventional 50:50 (by weight) part A/part B mixture, for example, a part A and part B combination sold by Shin-Etsu Chemical Company, Ltd. under the trademark KE-1935. Residual hydride groups were present in this polymer slab.

A solution of toluene and a mixture of the isomers identified in Example 3, hereinafter referred to as UV2, was prepared. This solution had a concentration of UV-2 equal to 0.01 molar.

The slab was immersed in the solution at 60° C. for 24 hours. The treated slab was air dried in an oven at 80° C. for 6 hours and then scanned to determine the degree of transmittance at various wavelengths in the UV/visible range.

Thereafter, the slab was extracted with toluene at ambient temperature for 48 hours. After drying, this extracted slab was scanned at various wavelengths in the UV/visible range.

The treated slab provided 45% transmission at 424 nm, whereas the extracted slab provided 45% transmission at 422nm. The treated slab was effective in absorbing UV light.

The similarity of the light absorbing properties of the treated slab and the extracted slab indicates that the UV light absorbing component (UV-2) had become covalently bonded to the silicone polymer during the treating process.

EXAMPLE 5

Example 4 was repeated except that the mixture of isomers produced in Example 2, hereinafter referred to as UV-3, was used in place of UV-2 in the toluene solution.

The original slab provided 45% transmission at 422 nm, whereas the extracted slab provided 45% transmission at 421 nm. The treated slab was effective in absorbing UV light.

The similarity of the light absorbing properties of the treated slab and the extracted slab indicates that the UV-3 had become covalently bonded to the silicone polymer during the treating process.

EXAMPLE 6

Example 4 was repeated except that UV-4 was used in place of UV-2 in the toluene solution.

The treated slab provided 45% transmission at 426 nm, whereas the extracted slab provided 45% transmission at 421 nm. The treated slab was effective in absorbing UV light.

The similarity of the light absorbing properties of the treated slab and the extracted slab indicates that the UV-4 had become covalently bonded to the silicone polymer during the treating process.

EXAMPLE 7

Example 4 was repeated except that 2-hydroxy-4-acrylyl oxyethoxy-benzophenone (sold by American Cyanamid Company under the trademark UV-2098), hereinafter referred to as UV-5, was used in place of UV-2 in the toluene solution.

The treated slab provided 45% transmission at 390 nm, whereas the extracted slab provided 45% transmission at 382 nm. The treated slab was effective in absorbing UV light.

The similarity of the light absorbing properties of the treated slab and the extracted slab indicates that the UV-5 had become covalently bonded to the silicone polymer during the treating process. The relatively large difference in the light absorbing properties of the treated slab and the extracted slab may be attributable to the presence of non-bondable impurities in UV-5.

EXAMPLE 8 (Comparative)

Example 4 was repeated except that 2-(3'-t-butyl-2'-hydroxy-t-5'-methylphenyl)-5-chlorobenzotriazole (sold by Ciba-Gergy Corporation under the trademark Tinuvin-326), hereinafter referred to as UV-6, was used in place of UV-2 in the toluene solution. This UV light absorbing material does not include an unsaturated functional group capable of reacting with the excess hydride groups in the original slab.

The treated slab provided 45% transmission at 413 nm, whereas the extracted slab provided 45% transmission at 392 nm. The treated slab was substantially more effective than the extracted slab in absorbing UV light.

The substantial difference between the UV light absorbing capabilities of the treated slab and the extracted slab indicate that a substantial portion of the UV-6 added during the treating process had been extracted from the polymer during the extraction processing. It is believed that substantially no covalent bonding between the UV-6 and the polymer had occurred.

EXAMPLE 9 (COMPARATIVE)

Example 4 was repeated except that 2-(3', 5'-di-[1", 1"-dimethylpropyl]-2'-hydroxylphenyl)-5-benzotriazole (sold by Ciba-Geigy Corporation under the trademark Tinuvin-328), hereinafter referred to as UV-7, chemical name of T-328) was used in place of UV-2 in the toluene solution. This UV light absorbing material does not include an unsaturated functional group capable of reacting with the excess hydride groups in the original slab.

The treated slab produced 45% transmission at 404 nm, whereas the extracted slab provided 45% transmission at 383 nm. The treated slab was substantially more effective than the extracted slab in absorbing UV light.

The substantial difference between the UV light absorbing capabilities of the [reared slab and the extracted slab indicate that a substantial portion of the UV-7 added during the treating process had been extracted from the polymer during the extraction processing. It is believed that substantially no covalent bonding has occurred.

EXAMPLE 10 (COMPARATIVE)

Example 4 was repeated except that 2, 2′-dihydroxy-4-methoxybenzophenone (sold by American Cyanamide Company under the trademark Spectrasorb UV24N), hereinafter referred to as UV-8, was used in place of III in the toluene solution. This UV light absorbing material does not include unsaturated functional group capable of reacting with the excess hydride groups in the original slab.

The treated slab provided 45% transmission at 419 nm whereas the extracted slab provided 45% transmission at 386 nm. The treated slab was substantially more effective than the extracted slab in absorbing UV light.

The substantial difference between the UV light absorbing capabilities of the treated slab and the extracted slab indicates that a substantial portion of the UV-8 added during the treating process had been extracted from the polymer during the extraction processing. It is believed that substantially no covalent bonding between the UV-8 and the polymer had occurred.

The substantial differences in the light absorbing characteristics between the treated slabs illustrated in Examples 9 and 10 and the extracted slabs illustrated in Examples 9 and 10, respectively, demonstrate that it is very difficult, or even impossible, to precisely control the UV cutoffs of such treated materials, particularly in a mass production setting.

EXAMPLES 11 TO 21

A series of eleven (11) slabs of polymer as described in Example 4 were used for this study.

Individual toluene solutions containing 0.2% by weight of one of UV-2, UV-4 and UV-6 were prepared. In addition, toluene solutions containing 0.2% by weight of UV-2 and 0.8% by weight of one of UV-4 and UV-6 were prepared. A toluene solution containing 5% by weight of UV-4 was also prepared.

Each of five (5) of these slabs was treated with one of the individual toluene solutions (other than the 5% UV-4/toluene solution) overnight at ambient temperature.

Each of another five (5) of these slabs was treated with one of the individual toluene solutions (other than the 5% UV-4/toluene solution) as follows. The slab was immersed in the toluene solution and heated to 100° C. for four (4) hours. Thereafter, the slab was maintained at ambient temperature overnight.

One of the slabs was immersed in the 5% UV-4/toluene solution at ambient temperature over a weekend, about 64 hours. Thereafter, this slab was heated in an oven in air at 100° C. for four (4) hours. On cooling, excess UV-4 precipitated inside and outside the slab. The slab was then immersed in toluene and maintained at 100° C. for one (1) hour. The slab was then dried and scanned at various wavelengths in the UV/visible range.

Each of the slabs was refluxed with isopropyl alcohol for four (4) hours, air dried, refluxed with toluene for four (4) hours and air dried to remove any unbound UV light absorber. The extracted slabs were then scanned at various wavelengths in the UV/visible range.

All the extracted slabs were transparent. Transmission results at 390 nm for each of the extracted slabs were as follows.

| UV Absorber | % Transmission At 390 nm | |
|---|---|---|
| | 100° C. TREATMENT | Ambient TREATMENT |
| UV-4 | 5.2 | 9.3 |
| UV-2 + UV-4 | 3.1 | 9.0 |
| UV-2 | 0.4 | 0.8 |
| UV-6 | 49.1 | 50.6 |
| UV-2 + UV-6 | 35.7 | 25.5 |
| UV-4(5%) | 0.1 | — |

All the extracted slabs treated with only UV-2, UV-4 or a combination of UV-2 and UV-4 were provided with reasonable amounts of UV light absorbing constituent even though low concentrations of the UV light absorbing components were used.

The slabs which had been subjected to 100° C. achieved better UV cutoffs than the corresponding slabs treated only at ambient temperature.

The slabs containing UV-6 retain some amount of this UV light absorbing material, but did not retain nearly the amount of such material as the amounts of UV-2 and UV-4 which were retained.

While this invention has been described with respect to various specific examples and embodiments, it is to be understood that the invention is not limited thereto and that it can be variously practiced within the scope of the following claims.

What is claimed is:

1. A method for incorporating a UV light absorbing constituent into a polymer material which comprises:
   introducing a reactable UV light absorbing component including a functional group selected from the class consisting of functional silicon-bonded hydride groups and functional ethylenically unsaturated groups into a polysiloxane polymer which is solid and cross-linked and contains reactable groups selected from the class consisting of reactable silicon-bonded hydride groups and reactable ethylenically unsaturated groups; and, thereafter,
   subjecting said reactable UV light absorbing component to conditions effective to chemically react said reactable UV light absorbing component with said reactable groups of said polysiloxane polymer and form a polymer material to which is covalently bonded an effective amount of a UV light absorbing constituent derived from said reactable UV light absorbing component.

2. The method of claim 1 wherein said introducing and subjecting are effective to distribute said UV light absorbing constituent substantially uniformly throughout said polymer material.

3. The method of claim 1 wherein said reactable UV light absorbing component is present in a liquid during at least a portion of said introducing.

4. The method of claim 1 wherein said reactable groups are reactable silicon-bonded hydride groups and said reactable UV light absorbing component includes a functional ethylenically unsaturated group.

5. The method of claim 1 wherein said reactable UV light absorbing component includes at least one siloxane moiety effective to enhance the compatibility of said reactable UV light absorbing component with said silicone polymer relative to a substantially identical reactable UV light absorbing component without at least one siloxane moiety.

6. The method of claim 1 wherein said reactable UV light absorbing component is selected from benzotriazole derivatives and mixtures thereof.

7. The method of claim 1 wherein said subjecting is substantially ineffective to increase or decrease the degree of polymerization or the degree of cross-linking of said polysiloxane polymer.

8. The method of claim 1 wherein said polysiloxane polymer is an optically clear, platinum-catalyzed, addition cure, cross-linked polysiloxane polymer containing reactable silicon-bonded hydride groups, and said reactable UV light absorbing component is a benzotriazole derivative including a functional vinyl group.

9. The method of claim 8 which further comprises forming said polymer material into a lens.

10. A method for incorporating a UV light absorbing component into a polymeric material which comprises:
    contacting a reactable UV light absorbing component including a functional group selected from the class consisting of functional silicon-bonded hydride groups and functional ethylenically unsaturated groups with a polysiloxane polymer which is solid and cross-linked and which contains reactable groups selected from the class consisting of reactable silicon-bonded hydride groups and reactable ethylenically unsaturated groups at conditions effective to chemically react said reactable UV light absorbing component with the reactable groups of said polysiloxane polymer.

11. A method for incorporating a beneficial constituent into a polymer material which comprises:
    introducing a reactable beneficial component including a functional group selected from the class consisting of functional silicon-bonded hydride groups and functional ethylenically unsaturated groups into a polymeric material which is a cross-linked and solid polysiloxane including reactable groups selected from the class consisting of reactable silicon-bonded hydride groups and reactable ethylenically unsaturated groups; and, thereafter,
    subjecting said reactable beneficial component to conditions effective to chemically react said reactable beneficial component with said reactable groups of said polymeric material, thereby forming a polymer material to which is covalently bonded a beneficial constituent derived from said reactable beneficial component in an amount effective to provide a benefit to said polymer material.

12. The method of claim 11 wherein said introducing and subjecting are effective to distribute said beneficial constituent substantially uniformly throughout said polymer material.

13. The method of claim 11 wherein said reactable groups are silicon-bonded hydride groups.

14. The method of claim 11 wherein said conditions are ineffective to increase or decrease the degree of polymerization or the degree of cross-linking of said polysiloxane.

15. The method of claim 11 wherein said polymer material is optically clear, and which method further comprises forming said polymer material into a foldable intraocular lens.

16. The method of claim 11 wherein said beneficial constituent is effective to provide said polymer material with reduced reactivity relative to the reactivity of said polymeric material.

17. A method for incorporating a beneficial constituent into a polymer material which comprises:
    introducing a reactable beneficial component including a functional group selected from the class consisting of functional silicon-bonded hydride groups and functional ethylenically unsaturated groups into a polymeric material which is a solid and cross-linked polysiloxane containing reactable groups selected from the class consisting of reactable silicon-bonded hydride groups and reactable ethylenically unsaturated groups; and, thereafter,
    subjecting said reactable beneficial component to conditions effective to chemically react said reactable beneficial component with said reactable groups of said polymeric material, thereby forming a polymer material to which is covalently bonded a beneficial constituent derived from said reactable beneficial component in an amount effective to provide a benefit to said polymer material, provided that said subjecting is substantially ineffective to increase or decrease the degree of polymerization or the degree of cross-linking of said polymeric material, and said polymer material is utilized without further substantial polymerization or cross-linking.

* * * * *